United States Patent [19]

Parliment

[11] Patent Number: 4,496,600
[45] Date of Patent: Jan. 29, 1985

[54] FLAVORING WITH 2-MERCAPTOALKYL OXATHIOLANES AND OXATHIANES

[75] Inventor: Thomas H. Parliment, New City, N.Y.

[73] Assignee: General Foods Corporation, White Plains, N.Y.

[21] Appl. No.: 538,470

[22] Filed: Oct. 3, 1983

[51] Int. Cl.³ ................... A23L 1/231; C07D 327/04; C07D 327/06
[52] U.S. Cl. .................................. 426/535; 549/14; 549/30
[58] Field of Search ..................... 426/535; 549/14, 30

[56] References Cited

U.S. PATENT DOCUMENTS

| 4,031,257 | 6/1977 | Wilson et al. | 426/535 |
| 4,042,601 | 8/1977 | Wilson et al. | 549/14 |
| 4,262,030 | 4/1981 | Winter | 426/535 |
| 4,374,998 | 2/1983 | Boden | 549/30 X |

OTHER PUBLICATIONS

Chemical Abstracts Service Registry Handbook, No. Section, 1965-1971, Registry Nos. 5638-36-8; 5684-34-4; 5684-35-5; 5721-89-1; 5721-85-7 and 5809-84-7.

*Primary Examiner*—Joseph Golian
*Attorney, Agent, or Firm*—Sam D. Walker; Thomas R. Savoie; Daniel J. Donovan

[57] ABSTRACT

The present invention discloses novel mercaptoalkyl substituted oxathiolanes and oxathianes which may be used as flavoring composition for food.

7 Claims, No Drawings

FLAVORING WITH 2-MERCAPTOALKYL OXATHIOLANES AND OXATHIANES

FIELD OF THE INVENTION

A flavoring composition and aroma for foodstuff and a process for preparing the same.

BACKGROUND OF THE INVENTION

Various heterocyclic compounds having one sulfur atom and one oxygen atom, such as an oxathiolane or an oxathiane have been produced wherein said compounds have been used to modify or enhance the flavor and aroma of foodstuff and the like. For instance U.S. Pat. No. 4,031,257 by Wilson et al., issued June 21, 1977 discloses oxathio heteroxcylic compound having the following structure.

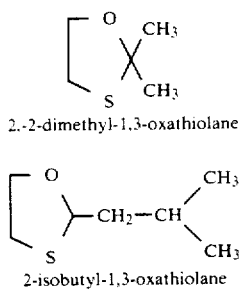

2,-2-dimethyl-1,3-oxathiolane 2-isobutyl-1,3-oxathiolane

Wherein the above structures enhances the fruit or vegetable taste or aroma of foodstuffs. Also U.S. Pat. No. 4,042,601 also by Wilson et al., issued Aug. 16, 1977 discloses one or more five or six membered oxathio heterocyclic compounds having one sulfur atom and one oxygen atom, such as oxathiolanes used to enhance the flavor and aroma of foodstuff.

The present invention discloses a new group of oxathiolanes, and oxathianes more particular mercaptooxathiolanes and mercaptooxathianes wherein said compounds have a meaty flavor and can be incorporated into other food products to impart acceptable flavors and aromas.

Therefore the object of the present invention is a new flavoring composition having a 5 or 6 membered oxathio heterocyclic mercaptan having two sulfur atoms and one oxygen atom and a process for preparing the same.

SUMMARY OF THE INVENTION

The present invention relates to mercapto substituted oxathiolanes and oxathianes as an aroma and flavor composition for food. More particular, the present invention discloses a flavor and aroma composition containing mercapto substituted oxathiolanes and oxathianes, and a method for imparting an odor and/or flavor to foodstuff using the same.

DETAILED DESCRIPTION OF THE INVENTION

The flavoring compositions produced in accordance with the present invention are mercapto substituted oxathiolanes and oxathianes having the following generic structure:

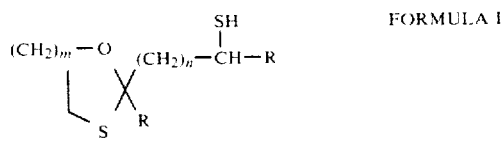

FORMULA I wherein:
each R is selected from the group consisting of H and hydrocarbon chain having from $C_1$ to $C_4$ carbon atoms;
$\eta$ is an integer from 0 to 3; and
m represent 1 or 2

When m is 1 the structures are referred to as oxathiolanes and are generally shown in FIG. II and when m is 2 the structures are referred to as oxathianes and are generally shown in Formula III.

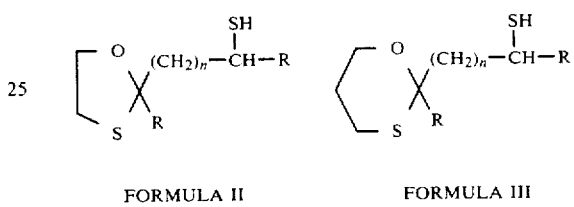

FORMULA II       FORMULA III

The oxatiolanes produced in accordance with the present invention can be prepared by reacting 1-mercapto-2-ethanol as shown in Formula IV with a mercaptocarbonyl as shown in Formula V.

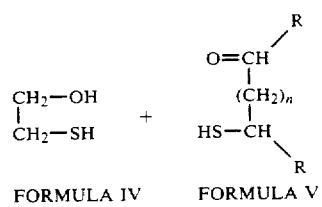

FORMULA IV       FORMULA V

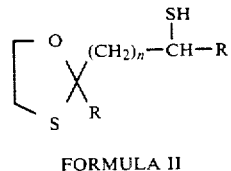

FORMULA II

For instance, when 1-mercapto-2-ethanol (Formula IV) is reacted with a mercaptocarbonyl such as 2-mercapto-3-butanone (Formula VI), 2-methyl-2-mercaptoethyl oxathiolane (Formula VII) is produced as set forth below.

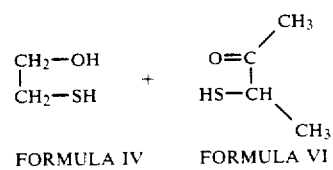

FORMULA IV       FORMULA VI

-continued

FORMULA VII

The oxathianes produced in accordance with the present invention can be prepared by reacting 1-mercapto-3-propanol (Formula IX) with a mercaptocarbonyl (Formula V).

FORMULA IX    FORMULA V

FORMULA III

For instance when 1-mercapto-3-propanol (Formula IX) is reacted with 2-mercapto-3-butanone (Formula VI) 2-methyl-2-mercaptoethyl oxathiane is produced as set forth below.

FORMULA IX    FORMULA VI

FORMULA X

The mercaptocarbonyls are prepared by the following procedure. First hydrogen sulfide is passed into a solution of sodium methoxide in methanol. The amount of sodium methoxide in methanol should be about 10% on a weight/volume basis. The hydrogen sulfide is passed into the sodium methoxide to form a sodium mercaptan complex. After the hydrogen sulfide addition is completed, a freshly distilled substituted halo carbonyl is added all at once with stirring. The reaction mixture is allowed to react for about 1 to 20 minutes, preferably for 5 minutes. The amount of the freshly distilled substituted halo carbonyl added should be equal to or less than the amount of sodium mercaptan, on a molar basis.

The freshly distilled substituted carbonyl reacts with the sodium mercaptan complex to form a mercaptocarbonyl having the following structure:

$$O=C-R$$
$$|$$
$$(CH_2)_n$$
$$|$$
$$HS-CH-R$$

wherein:
Each R is selected from the group consisting of H and a hydrocarbon chain having from $C_1$ to $C_4$ carbon atoms; and $\eta$ is an integer from 0 to 3.

The mercaptocarbonyl produced is then extracted into methylene chloride, and dried over sodium sulfate. Other solvents such as ethylene chloride benzene, toluene and the like may also be used.

To the mercaptocarbonyl produced in accordance with the above process, mercaptoalcohol is added in the presence of a catalyst. The mercaptocarbonyl and mercaptoalcohol should be combined at a molar ratio of 1 to 1, although one or the other can be employed in excess.

To produce an oxathiolane the length of the chain of the mercaptoalcohol is limited to 2 carbon atoms, such as 1-mercapto-2-ethanol (Formula IV). However, to produce an oxathiane which is a six membered ring the length of the chain of the mercaptoalcohol is limited to 3 carbon atoms such as 1-mercapto-3-propanol (Formula IX).

To drive the above reaction to completion at a very rapid rate, a catalyst is required. In the instant case p-toluensulfonic acid proves suitable. However other catalysts such as Aluminum Chloride, Boron Trifluoride Etherate, a Sulphonic acid ion exchange resin and the like can also be utilized. The amount of catalyst added should range from 0.005 to 5% depending on the reactant and the rate of reaction desired.

The mixture of mercaptocarbonyl and mercaptoalcohol are heated under reflux conditions, that is, to heat so that the vapors formed condense and return to be heated once again. The desired flavoring composition is produced by heating under reflux condition for a time period ranging from 10 to 120 minutes. It is preferred however, to reflux for about 40 minutes. The reaction is monitored by gas chromatography.

The resulting flavor composition namely an oxathiolane or an oxathiane is washed, dried and concentrated utilizing known procedures. The product may then be purified by established techniques such as preparative scale gas chromatography or distillation.

The mercapto substituted oxathiolanes and oxathianes produced have a meaty flavor. However, the oxathiolanes or oxathianes are distinguished by particular flavor and aroma based on the mercaptoketone that is heated with the mercaptoalcohol. For example 2-methyl-2-mercaptoethyl oxathiolane at levels of from 0.1 to 50 ppm produces flavor notes described as having a meaty character such as pork-meaty, brothy, and onion gravy.

The mercapto substituted oxathiolanes of Formula I and the mercapto substituted oxathiane of Formula III can be used as aromas and flavors for foodstuff such as soups, vegetables, sauces etc. The pronounced flavor of these compounds enable their use in finished products at very low levels such as 0.1 to 50 ppm. The mercapto substituted oxathiolanes of Formula I and the mercapto substituted oxathianes of Formula III can also be mixed with other carrier materials and/or diluents. If desired the mercapto substituted oxathiolanes and mercapto substituted oxathianes may also be mixed with other flavor-imparting ingredients to form aroma or flavor agent which may be conferred to foodstuff or which may intensify such flavor. The mercapto substituted oxathiolanes and oxathianes can be formulated as liquids, pastes or powder. The products can, for example, be spray-dried or vacuum dried. The mercapto substituted oxathiolanes and oxathianes produced are particularly applicable as a flavor source in food products such as texturized vegetable proteins or similar meat analog type products.

The following examples are given by way of illustration only and is not to be construed as limiting the invention in any way.

EXAMPLE I

Add 1.0 gram sodium methoxide to 30 ml. methanol. Pass hydrogen sulfide into the above mixture for 15 minutes to form a sodium mercaptan complex. To this mixture was added 2.0 grams of freshly distilled 2-chloro-3-butanone all at once with stirring. After 5 minutes dilute the mixture with 15 grams of water and extract the 2-mercapto-3-butanone into methylene chloride. The organic solution was then dried over sodium sulfate. To the 2 mercapto-3-butanone solution was added 1.4 grams of mercaptoethanol and 50 mg of p-toluene sulfonic acid (as catalyst). The mixture was then refluxed for 40 minutes. The resulting product was washed with sodium bicarbonate, dried and concentrated on a rotary evaporator. The material was then vacuum distilled to produce a water white solution having a boiling point from 60°–80° C. at 0.4 mm Hg, and possessing a desirable meaty, porky character. Infrared, NMR, and mass spectral analysis were all consistent with

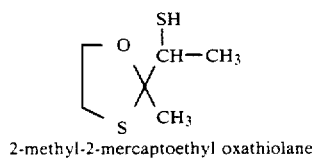

2-methyl-2-mercaptoethyl oxathiolane

EXAMPLE II

Add 1.0 gram sodium methoxide to 30 ml. methanol. Pass hydrogen sulfide into the above mixture for 15 minutes to form a sodium mercaptan complex. To this mixture is added 2.0 grams of freshly distilled 2-chloro-4-pentanone all at once with stirring. After 5 minutes dilute the mixture with 15 grams of water and extract the 2-mercapto-4-pentanone into methylene chloride. The organic solution is then dried over sodium sulfate. To the 2-mercapto-4-pentanone solution is added 1.4 grams of mercaptoethanol and 50 mg of p-toluene sulfonic acid (as catalyst). The mixture is then refluxed for 40 minutes. The resulting product is washed with sodium bicarbonate, dried and concentrated on a rotary evaporator. Final purification is achieved by preparative scale gas chromatography. The product is found to possess a desirable meaty, savory, character. Infrared, NMR, and mass spectral analysis are all consistent with

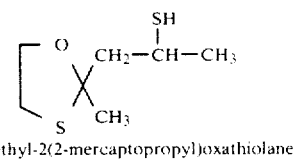

2-methyl-2(2-mercaptopropyl)oxathiolane

EXAMPLE III

Add 1.0 gram sodium methoxide to 30 ml. methanol. Pass hydrogen sulfide into the above mixture for 15 minutes to form a sodium mercaptan complex. To this mixture is added 2.0 grams of freshly distilled 3-chlorobutanal all at once with stirring. After 5 minutes dilute the mixture with 15 grams of water and extract the 3-mercaptobutanal into methylene chloride. The organic solution is then dried over sodium sulfate. To the 3-mercaptobutanal solution is added 1.4 grams of mercaptoethanol and 50 mg of p-toluene sulfonic acid (as catalyst). The mixture is then refluxed for 40 minutes. The resulting product is washed with sodium bicarbonate, dried and concentrated on a rotary evaporator. Final purification is achieved by preparative scale gas chromatography. The product is found to possess a desirable meaty, porky character. Infrared, NMR, and mass spectral analysis are all consistent with

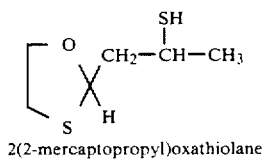

2(2-mercaptopropyl)oxathiolane

EXAMPLE IV

Add 1.0 gram sodium methoxide to 30 ml. methanol. Pass in hydrogen sulfide for about 15 minutes until sodium mercaptan has formed. Add 2.0 gm freshly distilled 2-chloro-3-butanone all at once with stirring. Dilute the mixture with 15 grams water and extract the 2-mercapto-3-butanone with methylene chloride. Back wash the organic solution with water and dry the organic solution over sodium sulfate. Add 1.4 gms mercaptopropanol and 50 mg p-toluene sulfonic acid to the mercaptoketone solution and reflux the solution for 30 minutes. After reaction is complete, wash the organic solution with aqueous sodium bicarbonate dry the solution and remove the solvent under vacuum. Final purification is achieved by preparative scale gas chromatography to yield:

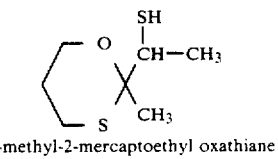

2-methyl-2-mercaptoethyl oxathiane

EXAMPLE V 1.0 gram sodium methoxide was added to 30 ml. methanol. Hydrogen sulfide was passed in for about 15 minutes until sodium mercaptan was formed. 2.0 gm freshly distilled 2-chloro-4-pentanone was added all at once with stirring. The mixture was diluted with 15 gms water and the 2-mercapto-4-pentanone was extracted with methylene chloride. The organic solution was back washed with water and dried over sodium sulfate. 1.4 gms mercaptopropanol and 50 mg p-toluene sulfonic acid were added to the mercaptoketone solution and the solutions were refluxed for 30 minutes. After reaction was completed, the organic solution was washed with aqueous sodium bicarbonate and dried and the solvent was removed under vacuum. Final purification was achieved by preparative scale gas chromatography to yield:

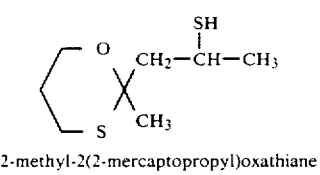

2-methyl-2(2-mercaptopropyl)oxathiane

EXAMPLE VI

Add 1.0 gram sodium methoxide to 30 ml. methanol. Pass in hydrogen sulfide for about 15 minutes until sodium mercaptan has formed. Add 2.0 gm freshly distilled 3-chlorobutanal all at once with stirring. Dilute the mixture with 15 gms water and extract the 3-mercaptobutanal with methylene chloride. Back wash the organic solution with water and dry the organic solution over sodium sulfate. Add 1.4 gms mercaptopropanol and 50 mg p-toluene sulfonic acid to the mercaptoaldehyde solution and reflux the solution for 30 minutes. After reaction is complete, wash the organic solution with aqueous sodium bicarbonate dry the solution and remove the solvent under vacuum. Final purification is achieved by preparative scale gas chromatography to yield:

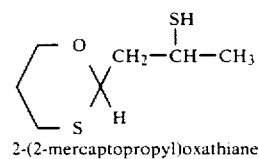

2-(2-mercaptopropyl)oxathiane

The flavoring composition produced according to Examples I to VI were dissolved in ethanol to form a 10% weight/weight solution. An aqueous solution containing 0.1, 1.0 and 10 ppm were evaluated by a taste pannel. The flavors were described as having a meaty, savory, buttery character.

What is claimed is:

1. A foodstuff containing a compound having a structure selected from the group consisting of:

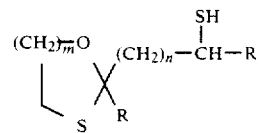

wherein:
each R is independently selected from the group consisting H and a hydrocarbon chain having from $C_1$ to $C_4$ carbon atoms;
$\eta$ is an integer from 0 to 3; and
m represents 1 or 2,
wherein the compound is in an amount of 0.1 to 50 ppm on an as-consumed foodstuff basis.

2. A foodstuff according to claim 1 wherein the composition is 2-methyl-2-mercaptoethyl oxathiolane.

3. A foodstuff according to claim 1 wherein the composition is 2-methyl-2(2-mercaptopropyl)oxathiolane.

4. A foodstuff according to claim 1 wherein the composition is 2(2-mercaptopropyl)oxathiolane.

5. A foodstuff according to claim 1 wherein the composition is 2-methyl-2-mercaptoethyl oxathiane.

6. A foodstuff according to claim 1 wherein the composition is 2-methyl-2(2-mercaptopropyl)oxathiane.

7. A foodstuff according to claim 1 wherein the composition is 2(2-mercaptopropyl)oxathiane.

* * * * *